US009693816B2

(12) United States Patent
Orszulak

(10) Patent No.: US 9,693,816 B2
(45) Date of Patent: Jul. 4, 2017

(54) ELECTROSURGICAL APPARATUS WITH INTEGRATED ENERGY SENSING AT TISSUE SITE

(75) Inventor: James H. Orszulak, Nederland, CO (US)

(73) Assignee: COVIDIEN LP, Mansfield, MA (US)

( * ) Notice: Subject to any disclaimer, the term of this patent is extended or adjusted under 35 U.S.C. 154(b) by 851 days.

(21) Appl. No.: 13/360,925

(22) Filed: Jan. 30, 2012

(65) Prior Publication Data

US 2013/0197503 A1 Aug. 1, 2013

(51) Int. Cl.
*A61B 18/12* (2006.01)
*A61B 18/14* (2006.01)
*A61B 18/00* (2006.01)

(52) U.S. Cl.
CPC ...... *A61B 18/1206* (2013.01); *A61B 18/1445* (2013.01); *A61B 2018/00095* (2013.01); *A61B 2018/00755* (2013.01); *A61B 2018/00791* (2013.01); *A61B 2018/00827* (2013.01); *A61B 2018/00892* (2013.01); *A61B 2018/00988* (2013.01)

(58) Field of Classification Search
CPC ............ A61B 18/1206; A61B 18/1445; A61B 2018/00095; A61B 2018/00755; A61B 2018/00827; A61B 2018/00892; A61B 2018/00988; A61B 2018/00791
USPC .................................. 606/33, 34; 607/33, 34
See application file for complete search history.

(56) References Cited

U.S. PATENT DOCUMENTS

| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |

(Continued)

FOREIGN PATENT DOCUMENTS

| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Lindsey G Wehrheim

(57) ABSTRACT

An electrosurgical system is disclosed. The system includes an electrosurgical instrument having at least one electrode configured as a first sensor for measuring a voltage drop therethrough and a temperature sensor for a thermal sensor configured to measure a temperature difference across the at least one electrode; and a generator including an output stage coupled to the at least one electrode, the output stage configured to generate radio frequency energy; and a controller configured to determine actual radio frequency current based on the voltage drop and electrical resistivity of the at least one electrode and radio frequency power based on the measured temperature difference and the thermal conductivity of the at least one electrode.

19 Claims, 10 Drawing Sheets

(56) References Cited

U.S. PATENT DOCUMENTS

| | | | |
|---|---|---|---|
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| 5,800,420 A * | 9/1998 | Gross | A61K 9/0021 204/280 |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| 6,083,223 A | 7/2000 | Baker | |
| 6,113,598 A | 9/2000 | Baker | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| 6,533,784 B2 | 3/2003 | Truckai et al. | |
| D493,888 S | 8/2004 | Reschke | |
| 6,786,905 B2 | 9/2004 | Swanson et al. | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,070,597 B2 | 7/2006 | Truckai et al. | |
| 7,083,619 B2 | 8/2006 | Truckai et al. | |
| D531,311 S | 10/2006 | Guerra et al. | |
| 7,115,139 B2 | 10/2006 | McClurken et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al | |
| D545,432 S | 6/2007 | Watanabe | |
| D547,154 S | 7/2007 | Lee | |
| 7,329,257 B2 | 2/2008 | Kanehira et al. | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,731,717 B2 | 6/2010 | Odom et al. | |
| D621,503 S | 8/2010 | Otten et al. | |
| 7,780,662 B2 | 8/2010 | Bahney | |
| 7,819,865 B2 | 10/2010 | Orszulak | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,901,400 B2 | 3/2011 | Wham et al. | |
| 7,931,649 B2 | 4/2011 | Couture et al. | |
| 7,985,220 B2 | 7/2011 | Orszulak | |
| D649,249 S | 11/2011 | Guerra | |
| D649,643 S | 11/2011 | Allen, IV et al. | |
| 2003/0078578 A1 | 4/2003 | Truckai et al. | |
| 2003/0171747 A1 | 9/2003 | Kanehira et al. | |
| 2003/0229344 A1 | 12/2003 | Dycus et al. | |
| 2004/0078035 A1 | 4/2004 | Kanehira et al. | |
| 2005/0033278 A1 | 2/2005 | McClurken et al. | |
| 2005/0197659 A1 | 9/2005 | Bahney | |
| 2005/0203504 A1 | 9/2005 | Wham et al. | |
| 2005/0283148 A1 | 12/2005 | Janssen et al. | |
| 2006/0224152 A1 * | 10/2006 | Behnke | A61B 18/1206 606/34 |
| 2007/0062017 A1 | 3/2007 | Dycus et al. | |
| 2007/0173811 A1 | 7/2007 | Couture et al. | |
| 2008/0039836 A1 | 2/2008 | Odom et al. | |
| 2008/0046122 A1 | 2/2008 | Manzo et al. | |
| 2008/0147057 A1 * | 6/2008 | Eisele | A61B 18/1206 606/34 |
| 2008/0195093 A1 | 8/2008 | Couture et al. | |
| 2009/0157071 A1 | 6/2009 | Wham et al. | |
| 2009/0157072 A1 | 6/2009 | Wham et al. | |
| 2009/0157075 A1 | 6/2009 | Wham et al. | |
| 2009/0204114 A1 | 8/2009 | Odom | |
| 2009/0248007 A1 | 10/2009 | Falkenstein et al. | |
| 2009/0248013 A1 | 10/2009 | Falkenstein et al. | |
| 2009/0248019 A1 | 10/2009 | Falkenstein et al. | |
| 2009/0248020 A1 | 10/2009 | Falkenstein et al. | |
| 2009/0248022 A1 | 10/2009 | Falkenstein et al. | |
| 2009/0254080 A1 | 10/2009 | Honda | |
| 2010/0016857 A1 | 1/2010 | McKenna et al. | |
| 2010/0063500 A1 | 3/2010 | Muszala | |
| 2010/0076427 A1 | 3/2010 | Heard | |
| 2010/0076431 A1 | 3/2010 | Allen, IV | |
| 2010/0076432 A1 | 3/2010 | Horner | |
| 2010/0087816 A1 | 4/2010 | Roy | |
| 2010/0094271 A1 | 4/2010 | Ward et al. | |
| 2010/0179545 A1 | 7/2010 | Twomey et al. | |
| 2010/0217264 A1 | 8/2010 | Odom et al. | |
| 2010/0286691 A1 | 11/2010 | Kerr et al. | |
| 2010/0312235 A1 | 12/2010 | Bahney | |
| 2010/0319956 A1 | 12/2010 | Ballard et al. | |
| 2011/0175819 A1 | 7/2011 | Jeong et al. | |
| 2011/0190653 A1 | 8/2011 | Harper et al. | |

FOREIGN PATENT DOCUMENTS

| | | | |
|---|---|---|---|
| DE | 2514501 | 10/1976 | |
| DE | 2627679 | 1/1977 | |
| DE | 3423356 | 6/1986 | |
| DE | 3612646 | 4/1987 | |
| DE | 8712328 | 3/1988 | |
| DE | 4303882 | 8/1994 | |
| DE | 4403252 | 8/1995 | |
| DE | 19515914 | 7/1996 | |
| DE | 19506363 | 8/1996 | |
| DE | 29616210 | 1/1997 | |
| DE | 19608716 | 4/1997 | |
| DE | 19751106 | 5/1998 | |
| DE | 19751108 | 5/1999 | |
| DE | 19946527 | 12/2001 | |
| DE | 10045375 | 10/2002 | |
| DE | 10 2004 026179 | 12/2005 | |
| DE | 20 2007 009165 | 10/2007 | |
| DE | 20 2007 009317 | 10/2007 | |
| DE | 20 2007 016233 | 3/2008 | |
| DE | 19738457 | 1/2009 | |
| DE | 10 2008 018406 | 7/2009 | |
| EP | 1159926 | 12/2001 | |
| EP | 1201196 A1 | 5/2002 | |
| EP | 1 772 109 A1 | 4/2007 | |
| EP | 1820460 A2 | 8/2007 | |
| EP | 1902681 A1 * | 3/2008 | A61B 18/14 |
| EP | 1 958 583 A2 | 8/2008 | |
| EP | 1 990 019 A2 | 11/2008 | |
| EP | 2 147 649 A1 | 1/2010 | |
| EP | 2529687 A2 | 12/2012 | |
| JP | 61-501068 | 9/1984 | |
| JP | 6-502328 | 3/1992 | |
| JP | 5-5106 | 1/1993 | |
| JP | 5-40112 | 2/1993 | |
| JP | 6-030945 | 2/1994 | |
| JP | 6-121797 | 5/1994 | |
| JP | 6-285078 | 10/1994 | |
| JP | 6-343644 | 12/1994 | |
| JP | 6-511401 | 12/1994 | |
| JP | 7-265328 | 10/1995 | |
| JP | 8-56955 | 3/1996 | |
| JP | 8-317936 | 3/1996 | |
| JP | 8-289895 | 5/1996 | |

(56) References Cited

FOREIGN PATENT DOCUMENTS

| | | |
|---|---|---|
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001000444 A | 1/2001 |
| JP | 2001-29356 | 2/2001 |
| JP | 2001-128990 | 5/2001 |
| JP | 2001165612 A | 6/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2008068364 A | 3/2008 |
| JP | 2011-125195 | 6/2011 |
| SU | 401367 | 11/1974 |
| WO | WO 99/40861 | 8/1999 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2004/073490 A2 | 9/2004 |
| WO | WO 2005/110264 | 11/2005 |
| WO | 2008102154 A2 | 8/2008 |
| WO | WO 2008102154 A2 * | 8/2008 ............. A61B 18/12 |
| WO | 2009018409 A2 | 2/2009 |
| WO | WO 2009/124097 A1 | 10/2009 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed 6/920/00, Thomas P. Ryan.
U.S. Appl. No. 12/336,970, filed Dec. 17, 2008, Paul R. Sremcich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M: Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.

(56) References Cited

OTHER PUBLICATIONS

Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.

(56) References Cited

OTHER PUBLICATIONS

Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report from corresponding Application No. EP 13152674.1 dated Jun. 5, 2013.
European Search Report for EP 10 18 8338 dated Feb. 17, 2015.

* cited by examiner

ELECTROSURGICAL APPARATUS WITH INTEGRATED ENERGY SENSING AT TISSUE SITE

BACKGROUND

Technical Field

The present disclosure relates to an electrosurgical system and method for performing electrosurgical procedures. More particularly, the present disclosure relates to a system and method for transmitting electrosurgical radio frequency energy from an electrosurgical generator to a treatment site and sensor signals from the treatment site to the electrosurgical generator with reduced energy loss and tissue site energy control.

Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing electrodes). In addition, electrosurgical energy must be applied to the tissue under controlled conditions to ensure creation of an effective vessel seal.

Transmission of electrosurgical energy to the treatment site, namely from the electrosurgical generator to the instrument, is accomplished via an electrosurgical cable. During transmission an electrical field is generated through the cable and stray electrosurgical RF energy is typically emitted along the cable path, which tends to reduce treatment energy and generates RF noise. Moreover, the electrical fields may interfere with the operation of other electronic equipment in the surgical area, such as patient monitoring equipment.

SUMMARY

The present disclosure relates to transmission of electrosurgical radio frequency ("RF") energy and sensor signals. An electrosurgical cable is disclosed having close proximity electrical field coupling between a supply and return transmission leads. As used herein, the term "electrical field coupling" denotes electrical and electromagnetic fields generated by the transmission of RF energy. The coupling maximizes application of the RF energy delivered during surgery and minimizes the stray RF energy radiated by the supply and return leads. Close proximity electrical field coupling significantly reduces the electrical field via field cancellation thereby increasing patient and surgeon safety. Coupling provides a low loss inductive/capacitive ("LC") transmission medium via a three-dimensional geometric orientation of the supply and return leads. The geometric orientation affects LC reactive components and reduces uncontrolled capacitively coupled reactance caused by stray RF radiation. In particular, capacitive reactance is caused by an antenna effect (e.g., radiative discharge of stray RF energy in air) for transmission mediums shorter than half a wavelength. Therefore, the geometric cable orientation controls the loss of stray RF energy, which is contained to a predetermined level and also reduces capacitive loading to the energy source (e.g., electrosurgical energy).

In one aspect, an electrosurgical system is disclosed. The electrosurgical system includes an electrosurgical instrument having at least one electrode configured as a first sensor for measuring a voltage drop. The system also includes a generator having an output stage coupled to the at least one electrode and configured to deliver radio frequency energy thereto; and a controller configured to measure the delivered radio frequency current at the tissue site, wherein the controller is configured to determine actual radio frequency current based on a measurement of the radio frequency voltage drop and as a function of resistivity of the at least one electrode.

In another aspect, an electrosurgical system is disclosed. The system includes an electrosurgical instrument having at least one electrode configured as a first sensor for measuring a voltage drop at the at least one electrode and as a thermal sensor for measuring temperature difference. The system also includes a generator having an output stage coupled to the at least one electrode and configured to deliver radio frequency energy thereto; and a controller configured to measure delivered radio frequency voltage at the output stage, wherein the controller is configured to determine actual radio frequency power based on a temperature difference measurement of the at least one electrode and as a function of a thermal conductivity of the at least one electrode.

In another aspect, an electrosurgical system is disclosed. The electrosurgical system includes an electrosurgical instrument having at least one electrode including a first sensor configured in the at least one electrode, the first sensor configured to measure a voltage drop and a temperature difference at the at least one electrode. The system also includes a generator having an output stage configured to generate radio frequency energy; and a controller configured to measure the delivered radio frequency voltage at the tissue site, wherein the controller is configured to determine current based on the voltage drop and power based on a temperature difference, the controller further configured to calculate the actual delivered radio frequency voltage as a function of the calculated power and current.

Another aspect includes a method for controlling an electrosurgical system. The method includes delivering radio frequency energy to at least one electrode coupled to an electrosurgical generator; measuring a voltage drop at the at least one electrode configured as a voltage sensor; measuring current of the radio frequency energy; calculating radio frequency current as a function of the voltage drop; and adjusting output of the electrosurgical generator as a function of the measured radio frequency current.

In yet another aspect, a method for controlling an electrosurgical system is described. The method includes measuring and controlling the radio frequency voltage as a function of derived current and power through at least one electrode of an electrosurgical instrument, the electrosurgical instrument being coupled to a generator; the generator having an output stage configured to generate radio frequency energy; and a controller configured to monitor and adjust the delivered energy at the tissue site as a function of the measured radio frequency voltage.

Subsequently in another aspect, a method for controlling an electrosurgical system is described. The method includes measuring and controlling temperature at the tissue site as a function of at least one of derived current, power or voltage through at least one electrode of an electrosurgical instrument, the electrosurgical instrument being coupled to a generator; the generator having an output stage configured to generate radio frequency energy; and a controller configured to monitor and adjust delivered energy at the tissue site as a function of the measured temperature difference.

Additionally in yet another aspect, a method for controlling an electrosurgical system is described. The method includes measuring and controlling tissue impedance as a function of derived current and power through at least one electrode of an electrosurgical instrument, the electrosurgical instrument being coupled to the generator; the generator having an output stage configured to generate radio frequency energy; and a controller configured to monitor and adjust the delivered energy at the tissue site a function of the measured tissue impedance.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical systems and either an endoscopic instrument or an open instrument. It should also be appreciated that different electrical and mechanical connections and other considerations apply to each particular type of instrument.

The present disclosure provides for an electrosurgical transmission cable wound in a double helix having a proximal geometric relationship in three-dimensional physical space, to control the inductive and capacitive components of the transmission cable and significantly reduce the capacitive leakage due to RF radiation. The transmission cable according to present disclosure is wound in a double helix and minimizes the stray RF radiation by reducing the transmitting antenna effect for transmission mediums shorter than ½ wavelength.

Figure 1:
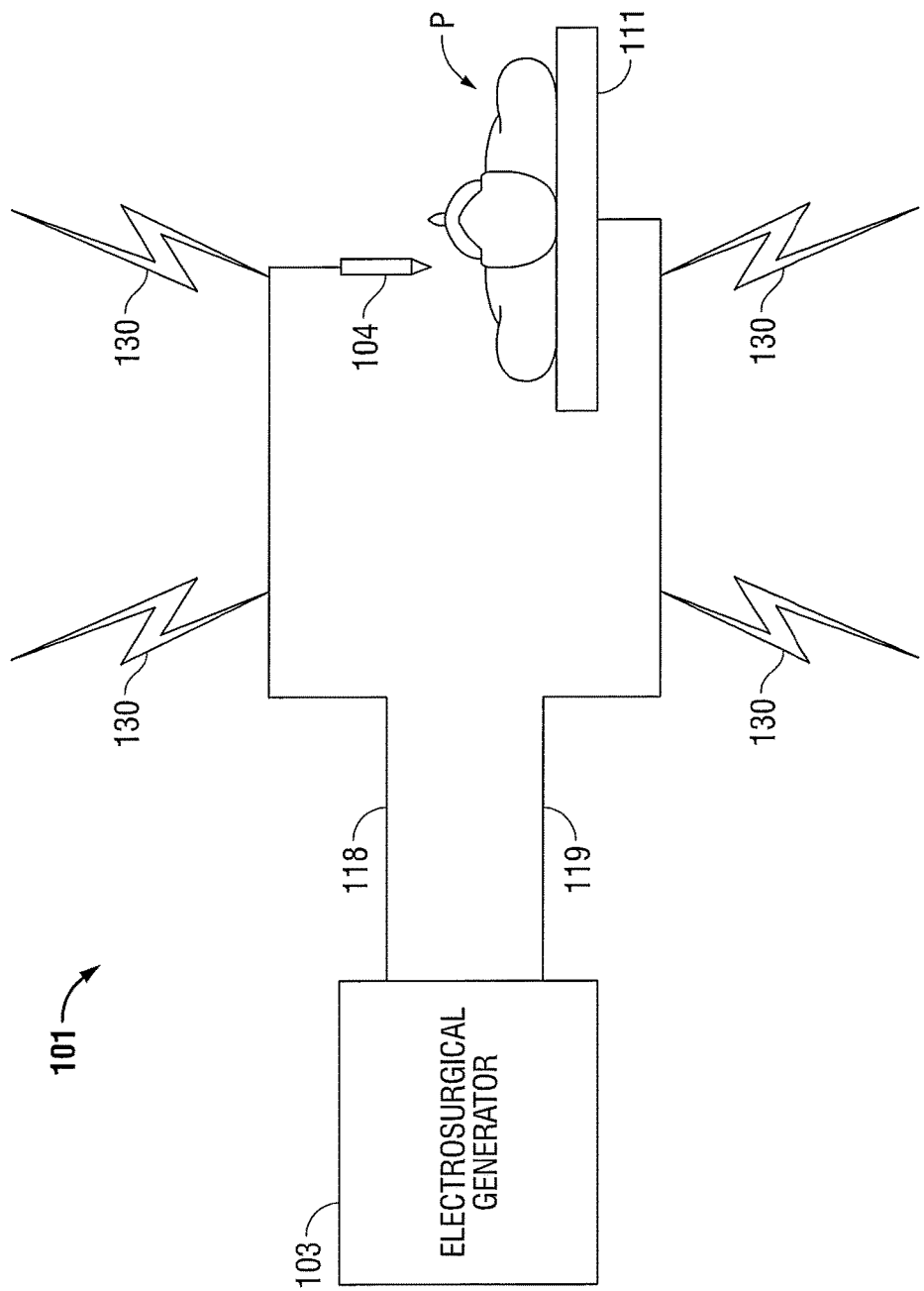
FIG. 1 is a schematic block diagram of a prior art electrosurgical system.

FIG. 1 is a schematic illustration of a prior art electrosurgical system 101. The system includes an electrosurgical generator 103 supplying electrosurgical radio frequency ("RF") energy to a monopolar electrosurgical instrument 104 via a supply transmission lead 118. The RF energy is returned to the generator 103 through a return electrode 111, shown as a return pad via a return transmission lead 119. Conventionally, the supply and return leads 118, 119 are oriented in a random fashion and thereby emit stray RF energy represented as uncontrolled radiation 130 due to RF energy flowing therethrough. In particular, random placement of the supply and return leads 118, 119 results in uncontrolled capacitive coupling due to stray RF radiation. RF radiation produces a transmitting antenna effect caused by random orientation of the supply and return leads 118, 119, which also generates an alternate RF leakage path for the RF energy.

Figure 2:
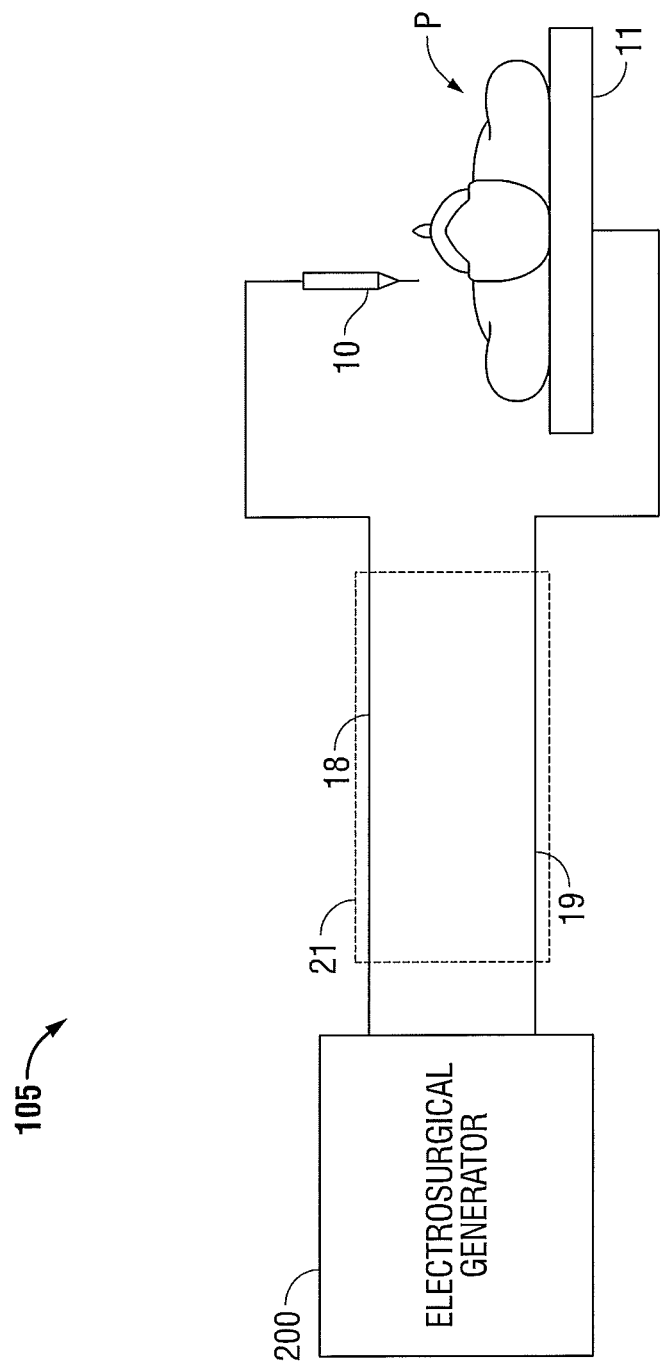
FIG. 2 is a schematic block diagram of an embodiment of an electrosurgical system according to the present disclosure.
Figure 4:
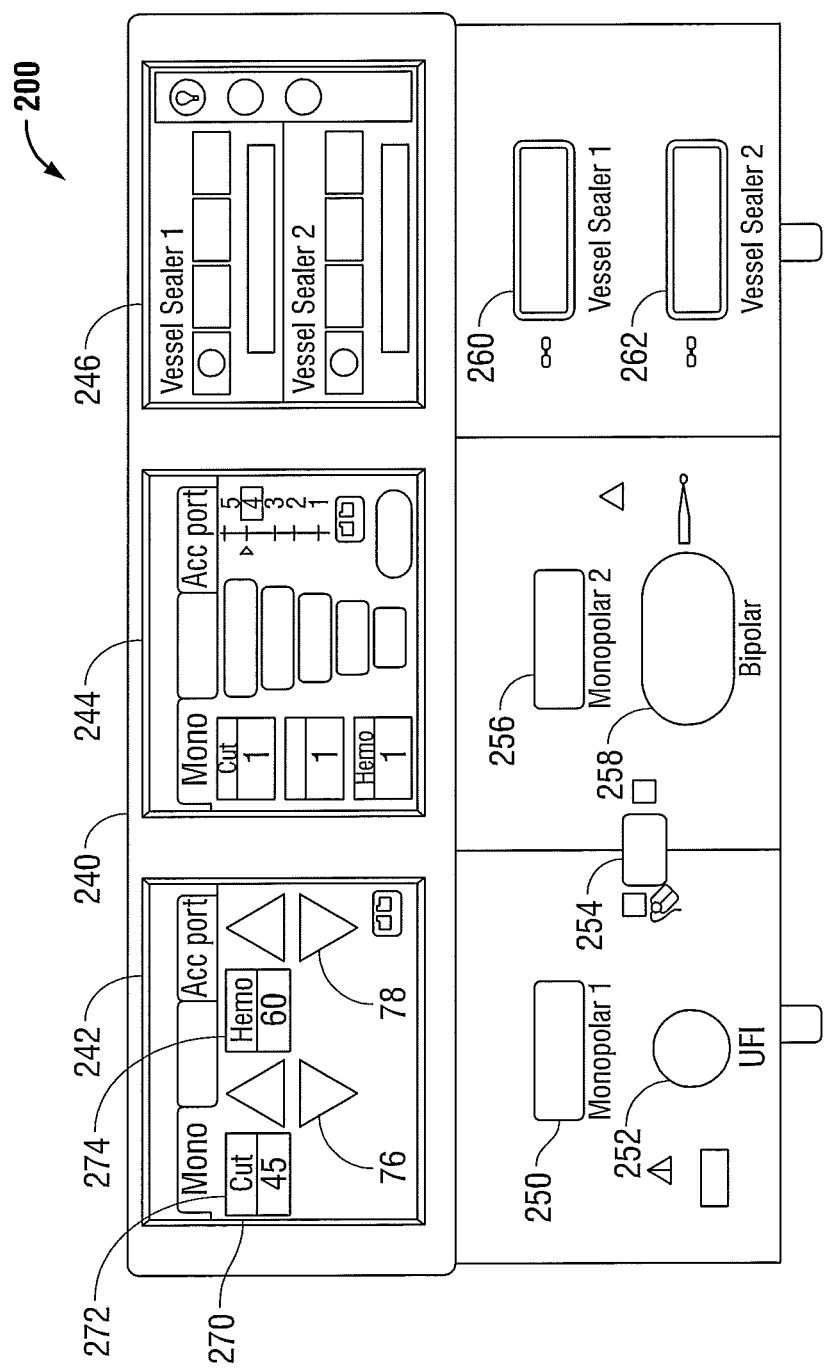
FIG. 4 is a front view of an electrosurgical generator according to the present disclosure.
Figure 5:
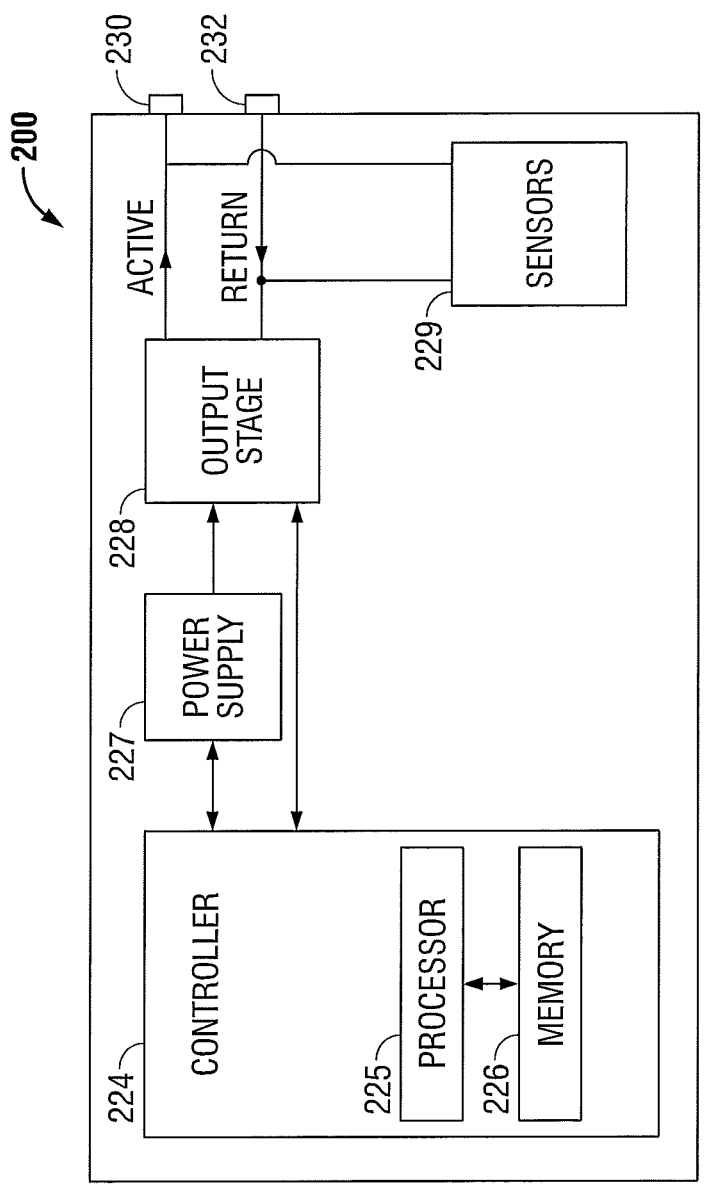
FIG. 5 is a schematic block diagram of the electrosurgical generator of FIG. 4 according to the present disclosure.

FIG. 2 is a schematic illustration of an electrosurgical system 102 according to the present disclosure. The system is a monopolar electrosurgical system that includes an electrosurgical instrument 10 having one or more electrodes for treating tissue of a patient P. With reference to FIGS. 2, 4, and 5, electrosurgical RF energy is supplied to the instrument 10 by a generator 200 via an active lead 18 that is operatively connected to an active output terminal 230 (FIG. 5) of the generator 200, allowing the instrument 10 to coagulate, cut, ablate and/or otherwise treat tissue. The supply and return leads 18, 19 are enclosed within a cable 21. The electrosurgical instrument 10 may be coupled to the generator 200 at a connector 250 or 256 (FIG. 4), each of which is coupled to the active terminal 230.

Energy is returned to the generator 200 through a return electrode 11 and transmitted through a return lead 19, which is operatively connected to a return output terminal 232 (FIG. 5) of the generator 200. The system 102 may include a plurality of return electrodes 11 that are disposed on a patient to minimize the chances of tissue damage by maximizing the overall contact area with the patient. The return electrode 11 may be coupled to the generator 200 at a connector 254 (FIG. 4), which is coupled to the return terminal 232. In embodiments, the generator 200 and the return electrode 11 may be configured for monitoring so-called "tissue-to-patient" contact to insure that sufficient contact exists therebetween to further minimize chances of tissue damage. The generator 200 may include a plurality of supply and return terminals and corresponding number of transmission cables (e.g., two of each).

Figure 3:
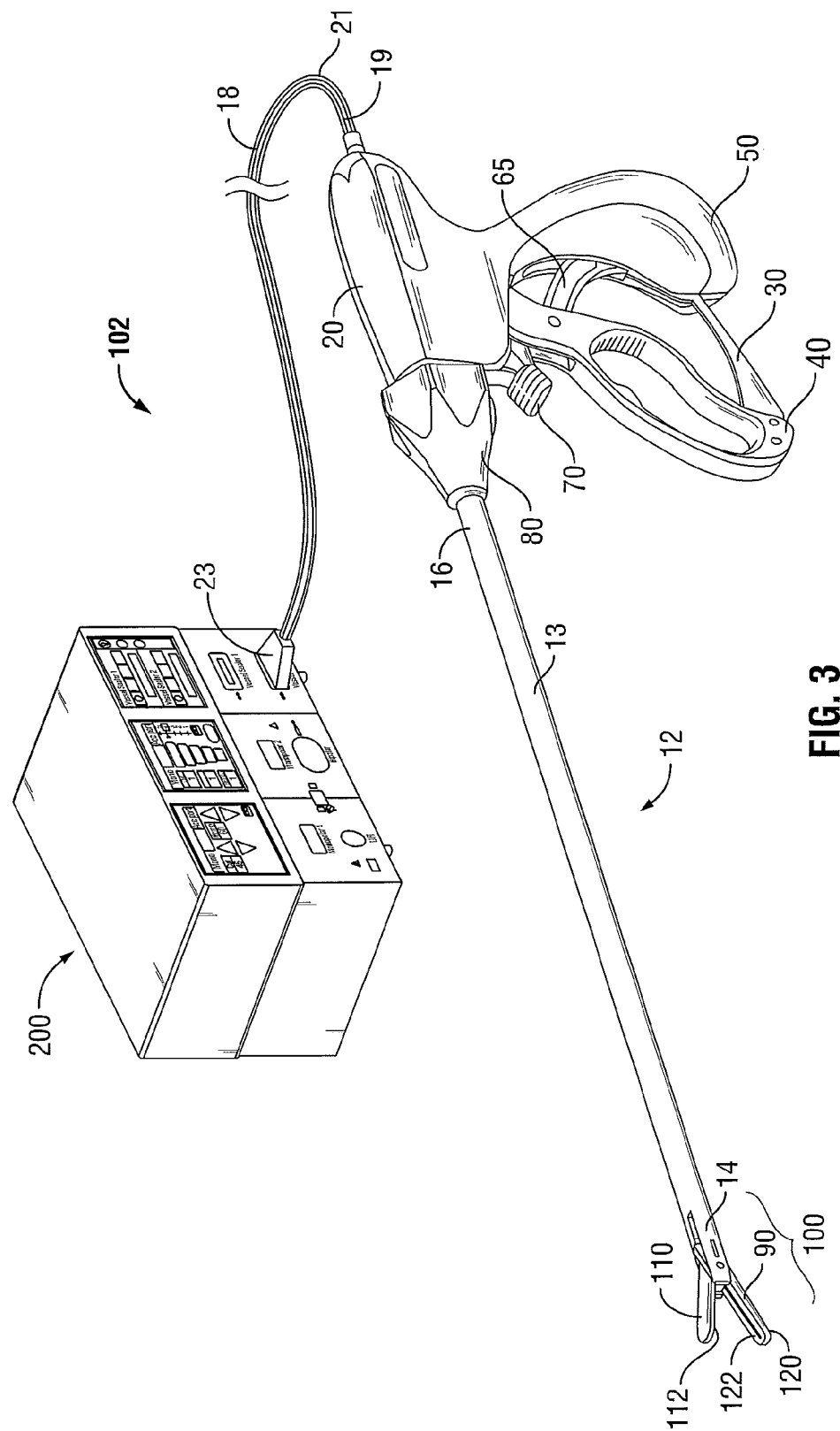
FIG. 3 is a perspective view of an embodiment of an electrosurgical system according to the present disclosure.

FIG. 3 shows a bipolar electrosurgical system 102 according to the present disclosure. The system 102 is a bipolar electrosurgical system that includes an electrosurgical forceps 10 having opposing jaw members 110 and 120. The forceps 10 is shown as an endoscopic version of a vessel sealing bipolar forceps. In embodiments, the forceps 10 may be any suitable electrosurgical sealing instrument, such as open-type forceps. The forceps 10 also includes a housing 20, a handle assembly 30, a rotating assembly 80, and a trigger assembly 70 which mutually cooperate with the end effector 100 to grasp, seal and, if required, divide tissue. Forceps 10 includes a shaft 13 having a distal end 14 that mechanically engages the end effector 100 and a proximal end 16 that mechanically engages the housing 20 proximate the rotating assembly 80. The end effector 100 includes two jaw members 110, 120 movable from a first position wherein the jaw members 110, 120 are spaced relative to on another to a closed position wherein the jaw members 110, 120 cooperate to grasp tissue therebetween. Each of the jaw members 110, 120 includes an electrode 112 and 122, respectively, forming an electrically conductive sealing surface connected to an energy source (e.g., a generator 200). The electrically electrodes 112 and 122 communicate electrosurgical energy through the tissue held therebetween. Electrosurgical RF energy is supplied to the forceps 10 by generator 200 via the active lead 18 operatively connected to the active electrode (e.g., sealing surface 112) and returned through the return lead 19 operatively connected to the return electrode (e.g., electrodes 122).

Handle assembly 30 includes a fixed handle 50 and a movable handle 40. Handle 40 moves relative to the fixed handle 50 to actuate the end effector 100 and enable a user to selectively grasp and manipulate tissue. The jaw members 110 and 120 move in response to movement of handle 40 from an open position to a closed position. In the open position, the electrodes 112 and 122 are disposed in spaced relation relative to one another. In a clamping or closed position, the electrodes 112 and 122 cooperate to grasp tissue and apply electrosurgical energy thereto. Jaw members 110 and 120 are actuated using a drive assembly (not shown) enclosed within the housing 20. The drive assembly cooperates with the movable handle 40 to impart movement of the jaw members 110 and 120 from the open position to the clamping or closed position. Examples of a handle assemblies are shown and described in commonly-owned U.S. application Ser. No. 10/369,894 entitled "Vessel Sealer And Divider And Method Manufacturing Same" and commonly owned U.S. application Ser. No. 10/460,926 entitled "Vessel Sealer And Divider For Use With Small Trocars And Cannulas."

The forceps 10 also includes a plug 23 that connects the forceps 10 to a source of electrosurgical energy, e.g., generator 200, via cable 21. With reference to FIGS. 3-5, the electrodes 112 and 122 are connected to the generator 200 through cable 21 that includes the supply and return leads 18, 19 coupled to the active and return terminals 230, 232 (FIG. 5), respectively. The electrosurgical forceps 10 is coupled to the generator 200 via the plug 23 at a connector 260 or 262 (FIG. 4), each of which is coupled to the active and return terminals 230 and 232 (e.g., pins, etc.).

With reference to FIGS. 4 and 5, front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read identifying information encoded on the plugs of the instruments (e.g., plug 23 of the forceps 10). The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-volatile memory, etc., which may then be coupled to or integrates into the plug. Corresponding detection devices may include, but are not limited to, bar code readers, electrical sensors, RFID readers, Hall Effect sensors, memory readers, etc. and any other suitable decoders configured to decode data encoded on the plug.

The generator 200 includes one or more display screens 242, 244, 246 for providing the user with variety of output information (e.g., intensity settings, treatment complete indicators, etc.). Each of the screens 242, 244, 246 is associated with a corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then inputs selections by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc., or sealing parameters, such as pressure, sealing duration, etc.

The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. In another embodiment, the generator 200 may be configured to output other types of energy such as, microwave, laser, etc. to power various other tissue treatment devices, such as microwave antennas, ultrasonic forceps, lasers, resistive heating electrodes, etc. The generator 200 includes a controller 224, a power supply 227 ("HVPS"), which may be a high voltage DC power supply, and an output stage 228. The HVPS 227 is connected to an AC source (e.g., electrical wall outlet) and provides high voltage DC power to an output stage 228, which then converts high voltage DC power into treatment energy (e.g., laser, ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which non-transitory storage medium readable by a computer (e.g., controller 224) and includes, but is not limited to non-volatile type memory, flash media, disk media, etc.). In embodiments, generator 200 may also include volatile type memory (e.g., RAM). The microprocessor 225 includes one or more output ports that are connected to the HVPS 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations discussed herein.

The generator 200 may also include a plurality of sensors 229 that provide feedback to the controller 224. In particular, the sensors 229 are configured to measure sourced RF current and voltage. The term "sourced" as used herein denotes the RF voltage and current of the RF waveform generated by the output stage 228 prior as measured prior to the RF waveform being transmitted through the cable 321. Such sensors are within the purview of those skilled in the art. The controller 224 then signals the HVPS 227 and/or output stage 228, which then adjusts the DC and/or power supply, respectively. The controller 224 also receives input signals from the input controls of the generator 200 or the forceps 10 and 100, as discussed above. The controller 224 utilizes the input signals to adjust the sourced power output by the generator 200 and/or performs other control functions thereon.

Figure 6:
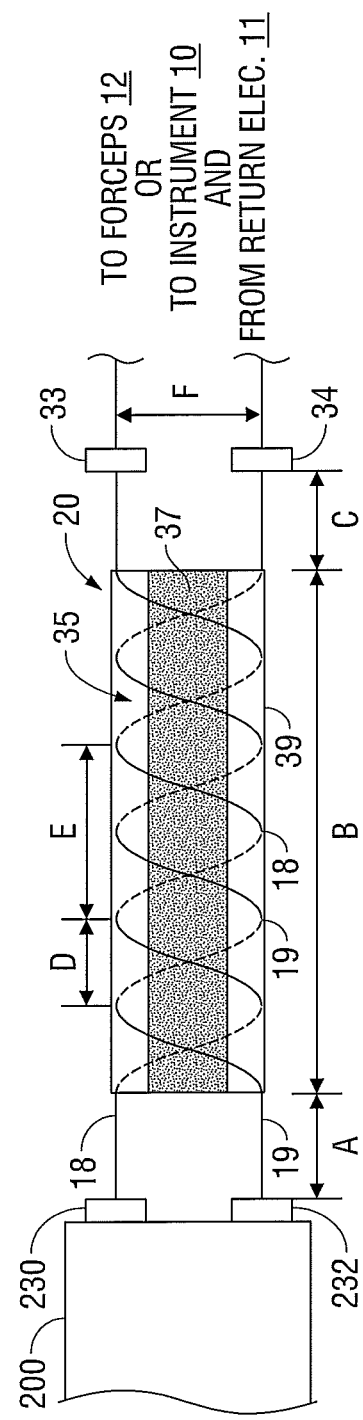
FIG. 6 is a cross-sectional schematic view of an electrosurgical cable according to the present disclosure.

FIG. 6 shows a cross-sectional view of the cable 21. Cable 21 includes the supply and return leads 18, 19 operatively connected to the generator 200 via active and return terminals 230, 232, respectively. Supply and return leads 18, 19 may be insulated. Various types of insulating materials may be used, which are within the purview of those skilled in the art. The supply and return leads 18, 19 extend from the active and return terminals 230, 232, respectively, for a distance A, which is optimally controlled by the location of active and return terminals 230, 232 and may be from about 0.1 inches to about 6 inches. Leads 18, 19 are then helix-wound in a wound portion 35, which may be from about 1 foot to about 20 feet, depending upon a desired cable inductance and capacitance. Alternatively, the wound portion 35 may extend from the active and return terminals 230, 232 without extending the supply and return leads 18, 19 for the distance A.

The wound portion 35, along cable length B, can be of any length depending on geometric configuration and physical properties (e.g., tensile strength, flexibility, etc.) of materials used in manufacturing of cable components. More specifically, leads 18, 19 are oriented in a double helix which includes two congruent helixes with the same axis, differing by a translation along the axis. The leads 18, 19 may be oriented in a plurality of other arrangements which wrap the leads 18, 19 around themselves. The arrangement of the leads 18, 19 in a double helix orients the opposing electrical fields generated by the electrosurgical RF energy passing therethrough to mitigate and/or cancel out thereby minimizing the amount of lost stray electrical RF energy.

The distance D of the portion 35, represents the distance between one apex of one helix and a nearest apex of another helix, and may be about ½ inch. The distance E, which is the distance between two apexes of the same helix may be about 1 inch. The outer diameter F of the cable 21 may be about ⅜ of an inch.

Leads 18, 19 are wound within the cable 21 around a dielectric core 37, which provides support for the leads 18, 19. An insulative sheath 39 covers the leads 18, 19. Dielectric core 37 and the sheath 39 may be of the same type. Leads 18, 19 may include a conductive trace that has an inductance rating at about 473 kHz of about 7.37 μH and a capacitance at about 1 MHz of about 32.0 PF to yield a cable-self-resonance of about 10.4 MHz. Conductive trace configurations are application-dependent and may be optimized for desired current density and voltages.

Cable 21 as illustrated in FIG. 6, provides a transmission medium to deliver RF energy from the generator 200 to a tissue site. Cable 21 represents one embodiment for the RF transmission medium, which reduces the radiated RF electrical field and maximizes the applied clinical treatment energy delivered to the tissue site. The dimensions A, B, C, D, E and F of FIG. 6 form a unique proximal geometric relationship in three dimensional space to control the electrical field coupling between the active and return output terminals of the generator 200 to significantly reduce the Volts per meter electric field and amps per meter electromagnetic field radiation by field cancellation.

The physical dimensions A, B, C, D, E and F are interdependent and may be optimized to provide a low loss inductive and capacitive transmission medium, which in addition to controlling the electrical field, reduces uncontrolled capacitive coupling caused by stray RF radiation. In particular the following formulas (I) and (II) illustrate the interdependent relationship of dimensions A, B, C, D, E and F with respect to inductive and capacitive properties of the cable 21.

$$\text{Inductance} = B(10.16 \times 10^{-9}) \text{Ln} \ [(2 \times D)/d)] + 2(A+C) \quad \text{(I)}$$
$$(\mu\text{H/in for specified exemplary conductive wire})$$

$$\text{Capacitance} = [(B \times (0.7065 \times 10^{-12}))/\text{Ln} \ [(2 \times D)/d]] er \quad \text{(II)}$$

In formulas (I) and (II) "d" denotes diameter of the conductive wire (e.g., supply and return leads 18, 19), "er" denotes the dielectric constant of the insulator. Further, E=2×D, the ratio of E to D establishes a continuum of the helix configuration and F=k×E, where "k" is a constant from about 0.5 to about 1.5.

At the distal end of the portion 35, the leads 18, 19 are unwound and are operatively connected to device connectors 33, 34 respectively, which may be pins disposed within the instrument 10. Leads 18, 19 extend a distance C from the portion 35 to the connectors 33, 34 in an unwound state for approximately 2.5 feet for monopolar coagulation applications. In embodiments, the initial length A of the leads and the unwound state length C may be equal in length.

In bipolar electrosurgery, the connectors 33, 34 may be situated on the forceps 10. In monopolar surgery, the connector 33 is operatively connected to the instrument 10 and the connector 34 is connected to the return electrode 11. As discussed above, in situations where a plurality of return electrodes are used, the return lead 19 may split into a corresponding number of leads to operatively connect all of the return electrodes 11 to the generator 200. With monopolar surgery the length C for lead 18 may be of a length greater than 2.5 feet with a corresponding decrease in lead 19 to accommodate manipulation of surgical instrument in the operating site.

Cable 21 according to the present disclosure orients the supply and return leads 18, 19 so that the electrical fields generated therethrough are canceled, thereby reducing the amount of leaked stray RF energy. More specifically, placement and orientation of the leads 18, 19 in the manner discussed above provides for close proximity of electrical fields generated during transmission of electrosurgical RF energy and maximizes amount of energy delivered to the treatment site. Reducing the electrical fields also increases safety of personnel and the patient.

Reduced RF radiation decreases capacitive and RF field leakage and improves RF control of the delivered energy. Reduced RF radiation also decreases RF transmission loss and improves efficiency of the generator 200 by reducing the RF harmonic component, minimizing corruption of the RF source and reducing peripheral conductive and radiative emissions. Further, reducing RF radiation also decreases the RF noise to additional equipment found in the room, such as patient monitoring equipment.

In addition, the transmission system according to the present disclosure also provides novel ways to sense tissue and energy parameters directly at the tissue site. Conventional electrosurgical systems sense and control energy delivery at the power source and calibrate for the energy transmission losses, but cannot compensate for electrical field corruptive interference to the delivered energy. In particular, energy lost during transmission to and from the instrument as well as internal loss within the power source may only be approximated due to an electrical field interference. Thus, conventional electrosurgical system do not directly control energy applied to the tissue or monitor energy and tissue parameters at the tissue site, which may result in less than optimal tissue treatment.

The present disclosure provides a system for sensing tissue and energy parameters directly at the tissue site allowing for accurate feedback control of the applied energy to optimally achieve desired tissue treatment effect including, but not limited to, hemostasis, vessel sealing, and coagulation. In particular, the present disclosure includes sensors disposed at the treatment site for sensing various tissue and energy parameters and utilizes the transmission medium (e.g., cable 21) to minimize the voltage electric field and current electromagnetic field components and maximize the sensed signal integrity. The sensed signals are then transmitted to the power source without compensation for any loss or signal degradation due to conventional losses described above. A transmission medium cable for transmitting electrosurgical energy from a generator to an instrument is disclosed in a commonly-owned U.S. Pat. Nos. 7,819,865 and 7,985,220, entitled "Electrosurgical Radio Frequency Energy Transmission Medium," the entire contents of both of which are incorporated by reference herein.

Figure 7:
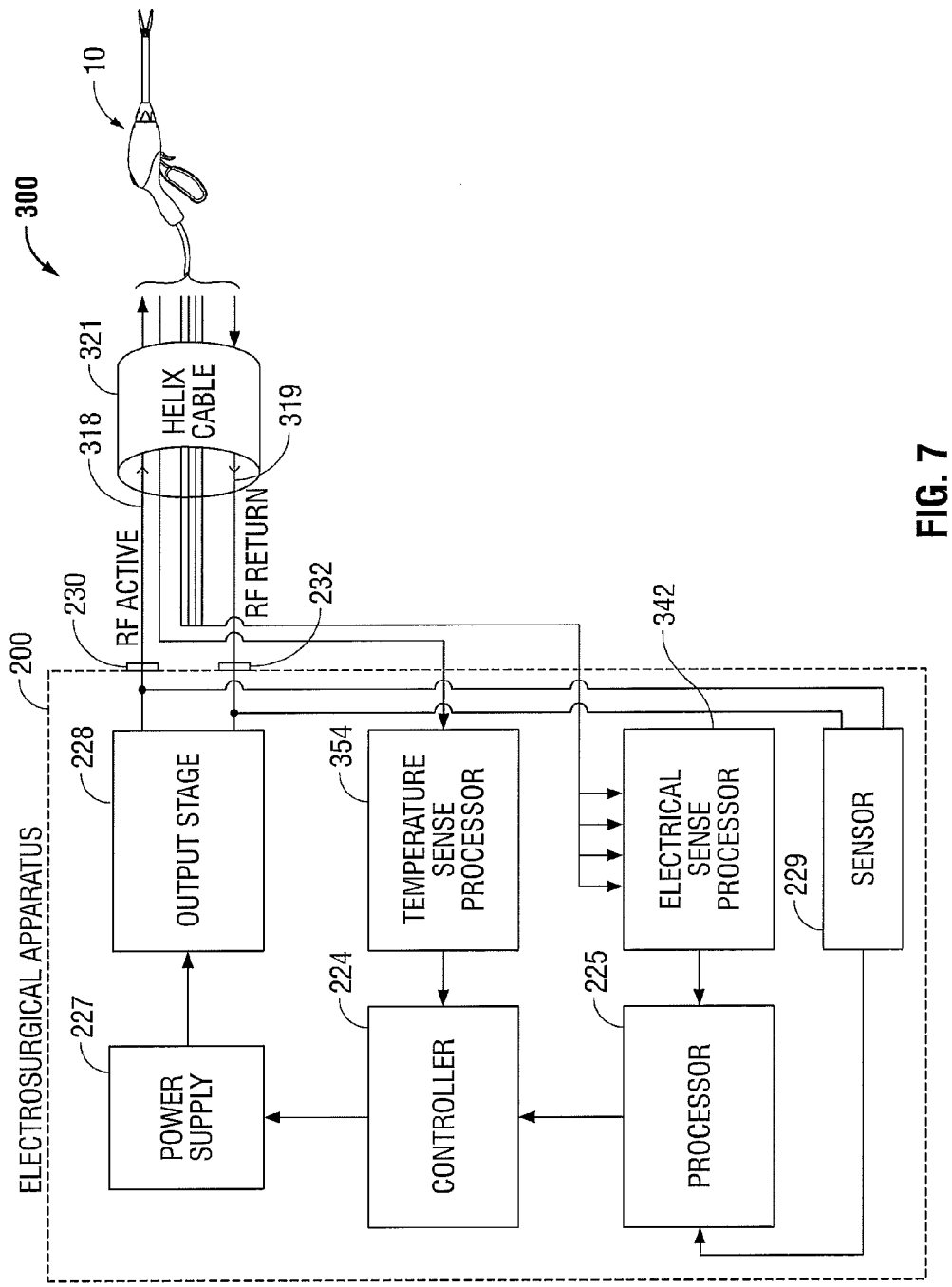
FIG. 7 is a schematic view of an electrosurgical system according to the present disclosure.
Figure 8:
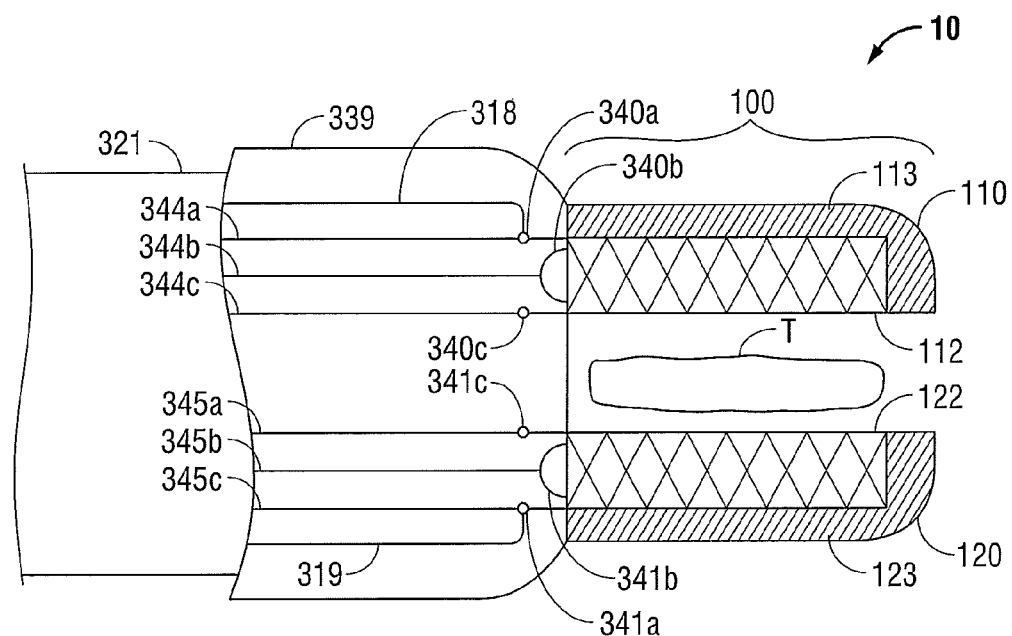
FIG. 8 is a schematic view of an end effector of the electrosurgical system of FIG. 7 according to the present disclosure.

FIG. 7 shows a system 300 including generator 200 and forceps 10. FIG. 8 shows schematically the end effector 100 including the pair of opposing jaw members 110 and 120 each having electrodes 112 and 122 disposed within jaw housings 113 and 123, respectively. The housings 113 and 123 may be formed by overmolding an insulative material over the electrodes 112 and 122 to isolate the applied electrical and thermal energy from adjacent tissue.

System 300 provides control of the treatment energy (e.g., output of the generator 200) in a closed loop manner based on the tissue and energy properties sensed directly at the tissue site. Parameters of the treatment energy which may be adjusted by the system 300 include, but are not limited to, energy, power, voltage, current, tissue impedance, rates of change of these parameters, and combinations thereof. Measured tissue properties include, but are not limited to, tissue impedance, tissue temperature, tissue hydrology, tissue vascularity, burst strength of sealed vessels, thermal spread, and combinations thereof. Measured energy properties include, but are not limited to voltage, current, power, phase, instantaneous, average, and root mean square values and combinations thereof.

The system 300 includes electrical sensors for detecting tissue and energy properties directly at the tissue site and transmitting the sensor measurements along electrical and/or optical cables to the generator 200. With reference to FIGS. 7 and 8, the electrical sensor leads 344a, 344b, 344c, 345a, 345b, 345c are disposed within a transmission medium (e.g., cable 321) of wound RF supply and return leads 318, 319 to minimize tissue site sensor signal degradation. In particular, the cable 321 allows for transmission of sensor signals from integrated energy-sensing elements disposed at the end effector 100 with minimal signal degradation. The system 300 utilizes the sensor signals in a closed loop manner to control application of treatment energy to achieve optimal tissue treatment effects.

Forceps 10 is coupled to the generator via the cable 321. Generator 200 includes the output stage 228 coupled to supply and return leads 318, 319 disposed within the cable 321. The supply and return leads 318, 319 are operatively connected to the generator 200 via active and return terminals 230, 232 respectively. The cable 321 is substantially similar to cable 21 described above with respect to FIG. 6, thus the embodiment of cable 21 is incorporated into the embodiment of cable 321 including, but not limited to, the elements of the cable 21, such as leads 18, 19, dielectric core 37, insulative sheath 38, and the like, as well configuration, arrangement, and material properties of these components.

Figure 9:
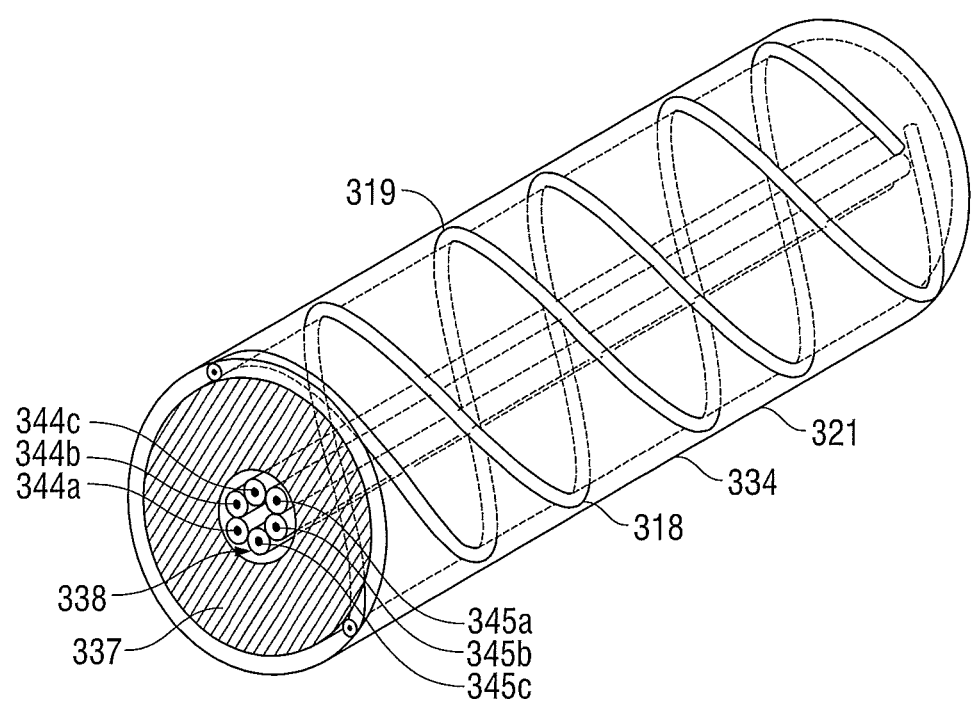
FIG. 9 is a cross-sectional, perspective view of an electrosurgical cable of FIG. 7 according to the present disclosure.

With respect to FIG. 9, cable 321 includes a dielectric core 337 forming the core of cable 321. Supply and return leads 318 and 319 are wound about dielectric core 337 in a double helix manner and arranged in similar configuration as leads 18 and 19 of FIG. 6. Dielectric core 337 has a substantially tubular structure having a lumen 338 defined therethrough. The arrangement of the leads 318, 319 in a double helix orients the opposing electrical fields generated by the electrosurgical RF energy passing therethrough to mitigate and/or cancel out thereby minimizing the amount of lost or stray electrical RF energy. Cable 321 also includes an insulative sheath 339 which is disposed over leads 318 and 319 thereby securing the leads 318 and 319 to the dielectric core 337.

Cable 321 as illustrated in FIG. 8, provides a transmission medium to deliver RF energy from the generator 200 to the tissue T grasped between the jaw members 110 and 120. Each of the jaw members 110 and 120 includes electrodes 112 and 122 which are configured as electrode sensors and electrodes for delivering RF energy to tissue. The electrodes include one or more connections 340a, 340c and 341a, 341c and thermal sensors 340b and 341b, respectively. The electrodes 112 and 122 are configured to measure properties of the RF energy delivered to the tissue T and may be any suitable electrical sensors including, but not limited to, conductive resistors, sense transformers, thermal impedance devices, composite materials having known conductive resistivity and thermal conductivity, and combination thereof. The electrodes 112 and 122 may be disposed in one or both of the jaw members 110 and 120 and are in electrical communication with the generator 200, respectively. This configuration allows the electrodes 112 and 122 to delivery RF energy and to detect electrical current voltage, phase and other properties of electrical energy passing directly through the electrodes 112 and 122 without measuring the current at the generator 200 as performed in conventional electrosurgical systems. The measured parameters may then be used to determine various tissue and energy as described in further detail below.

The electrodes 112 and 122 are formed from a substantially homogenous material having a known electrical resistivity, $\rho$, which may be from about $1.4 \times 10^{-3}$ Ohm per meter ($\Omega \cdot m$) to about $5 \times 10^{-3}$ $\Omega \cdot m$ and a known thermal conductivity, k, which may be from about 2.0 Watt/meter·Kelvin (W/m·K°) to about 7.0 W/m·K°.

The connections 340a, 340c, 341a, 341c are coupled to an electrical sense processor 342 via one or more electrical sensor leads 344a, 344c, 345a, 345c, respectively. As shown in FIGS. 8 and 9, the leads 344a, 344c, 345a, 345c are disposed within the cable 321 and pass through the lumen 338. The leads 344a, 344c, 345a, 345c may be insulated. Various types of insulating materials may be used, which are within the purview of those skilled in the art. Sense processor 342 is disposed within the generator 200 and is coupled to the controller 224 and/or the processor 225. Sense processor 342 receives the electrical sense signals from the electrodes 112 and 122 and determines tissue and/or energy parameters at the tissue T and then transmits the calculations to the controller 224 through the processor 225. In embodiments, the processor 225 may include or be coupled to an isolation circuit, e.g., optical isolators, to provide an isolation barrier between RF energy and protective earth ground for patient safety. In further embodiments, the connections 340a, 340c, 341a, 341c may be directly coupled to the controller 224 such that the controller 224 performs the functionality of the sense processor 342, namely, determination of tissue and energy parameters based on electrical sense signals.

As shown in FIG. 8, forceps 10 also includes one or more difference thermal sensors 340b and 341b disposed within the jaw members 110 and 120 and coupled to the electrodes 112 and 122, respectively. As used herein, the term "difference thermal sensor" denotes a sensor that measures the temperature difference across each of the electrodes 112 and 122. Suitable thermal sensors include, but are not limited to, electronic device thermal sensors, micro electro-mechanical thermal sensors, thermocouple devices, infrared devices, fiber optic thermal sensors such as Fiber Bragg gratings, and combinations thereof.

Thermal sensors 340b and 341b are coupled to a temperature sense processor 354 via one or more sensor leads 344b and 345b, respectively. The sensor leads 344b and 345b may be electrical, optical, or any other suitable connection leads. As shown in FIG. 9, the leads 344a and 345b are disposed within the cable 321 and pass through the lumen 338. Sense processor 354 is disposed within the generator 200 and is coupled to the controller 224 and/or the processor 225. Sense processor 354 receives the temperature sense signals from the sensors 340b and 341b and determines the temperature difference across each of the electrodes 112 and 122 and then transmits the calculations to the controller 224. In embodiments, the sense processor 354 may receive either temperature difference measurements or temperature measurements directly and then determine the temperature difference across each of the electrodes 112 and 122. In further embodiments, the sense processor 354 may also include or be coupled to an isolation circuit, e.g., optical isolators, to provide an isolation barrier between the RF energy and protective earth ground for patient safety. In further embodiments, the sensors 340b and 341b may be directly coupled to the controller 224 such that the controller 224 performs the functionality of the sense processor 354, namely, determination of sealing surface temperature based on electrical or optical sense signals.

In response to the electrical and temperature sense signals, the controller 224 may adjust the output of the generator 200. In embodiments, the controller 224 may include one or more algorithms for controlling the output as a function of the detected tissue and/or energy properties. In particular, the algorithm implemented in the controller 224 may drive the output of the generator 200 as well as its components, including the temperature sense processor 354 and the electrical sense processor 342 to continuously monitor tissue and/or energy properties for adjustment of the generator output.

Figure 10:
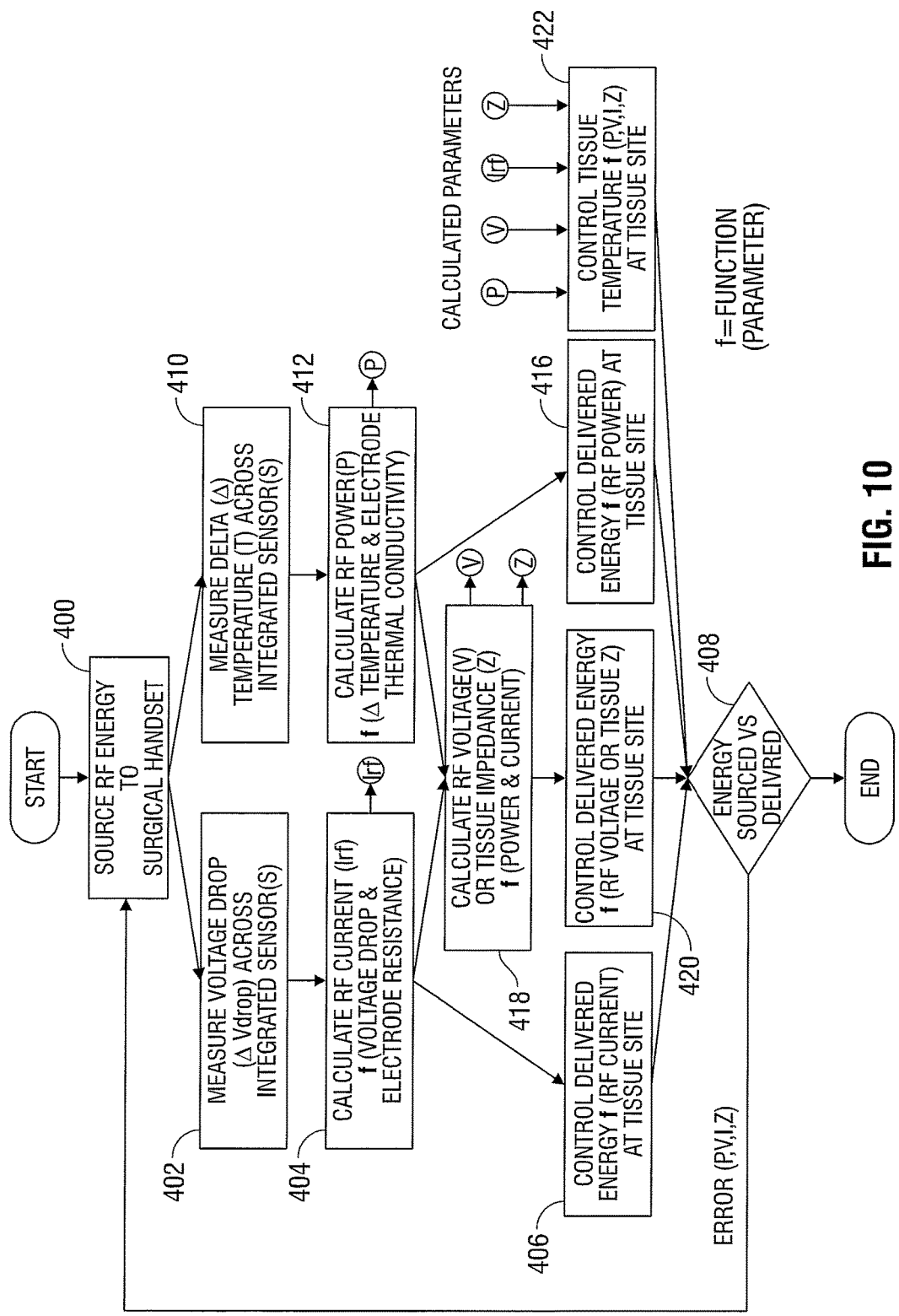
FIG. 10 is a flow chart diagram of a method according to the present disclosure.

FIG. 10 shows a method for monitoring tissue and controlling energy properties using the system 300 of FIG. 7. In step 400, the generator sources the radio frequency energy to the instrument 10 over the helix transmission cable 321 where the energy is delivered to the tissue site via electrodes 112 and 122. Sensor 229 monitors the sourced energy generated and provides input to controller 224, as it is transmitted over the helix cable.

In step 402, generator 200 measures the voltage drop $\Delta V_{drop}$ across each of the electrodes 112 and 122 via connections 340a, 340c, 341a, 341c, which is transmitted to controller 224 over an isolation barrier incorporated in the electrical sense processor of 342. Controller 224 receives the isolated voltage drop from 342 and calculates the RF current delivered to the tissue as a function of the electrical resistivity of the electrodes 112 and/or 122.

This determination may be performed by the controller in step 404 via the formula (III) below:

$$\text{RF current}(I_{rf}) = \Delta V_{drop}/R \quad \text{(III)}$$

In formula (III), R is electrode resistance, which may be calculated via the formula (IV)

$$R = [(\rho \cdot l)/A] \quad \text{(IV)}$$

In formula (IV) A is electrode area in meters squared, l is the electrode length in meters, $\rho$ is resistivity. The values A, l, and $\rho$ may be stored in the memory 226 such that the resistance R may be calculated for each instrument 10. It is envisioned that various instruments 10 may include electrodes 112 and 122 of various sizes, resistance, and other properties. These properties may be communicated to the generator 200 via identification systems discussed above or otherwise input by the user.

Controller 224 determines actual RF current and controls the delivered energy to the tissue site in step 406 as a function of the calculated actual RF current. Differences in the sourced energy sensed by the sensor 229 and the delivered energy as calculated by the controller 224 based on the voltage drop are adjusted in step 408, where an error signal is returned by the controller 224 to adjust RF output of the generator 200 by controlling the output stage 228 and/or the power supply 227. In step 400, the controller 224 corrects the delivered RF current for closed loop controlled delivery of the tissue treatment energy and effective hemostasis of tissue.

In step 410, which may be performed concurrently with the step 402, the generator 200 measures ΔT, the temperature difference across each of the electrodes 112 and 122 via thermal sensors 340b, 341b. The temperature difference signal is transmitted via leads 344b and 345b to controller 224 over an isolation barrier, incorporated in the temperature sense processor 354. Controller 224 receives the processed temperature difference from the processor 354 and calculates the RF power delivered to the tissue as a function of the thermal conductivity of the electrodes 112 and 122. This calculation is performed in step 412 using the formula (V) below:

$$\text{RF power}(P)=T/\Theta \qquad (V)$$

In formula (V), $\Theta$ is thermal impedance $\Theta$ (° C./Watt) which may also be expressed as thermal conductivity, k, [Watt/(m·K)], where K is temperature in degrees Kelvin, and m is meters. These values may be stored in the memory 226 as described above with respect to the resistivity, dimensions and other properties of the electrodes 112 and 122.

Controller 224 determines actual RF power and controls the delivered energy to the tissue site in step 416, as a function of the calculated actual RF power. Differences in the sourced energy as measured by the sensor 229 and the delivered energy are adjusted in step 408, where an error signal is returned by the controller 224 to adjust RF output of the generator 200 by controlling the output stage 228 and/or the power supply 227. In step 400, the controller 224 corrects the delivered RF power for closed loop controlled delivery of the tissue treatment energy and effective hemostasis of tissue.

As represented in formulas (III)-(V), ρ is the electrical resistivity and k is the thermal conductivity of the electrodes 112 and 122, $I_{rf}$ is the actual RF current delivered to the tissue as calculated in equation (III) and P is the actual RF power delivered to the tissue as calculated in equation (V). The electrical resistivity and thermal conductivity of the sealing electrodes 112 and 122 is stored in the memory of 226 as described above. In embodiments, the electrical resistivity and thermal conductivity may be pre-calculated based on the geometry of the electrodes 112 and 122 and its material properties or composition for a range of temperatures, which may be stored in a look-up table in the memory 226. In further embodiments, the electrical resistivity and thermal conductivity may be adjusted in real time as a function of the material characteristic temperature, also stored in memory 226, to compensate for electrode resistance R and thermal impedance changes due to temperature variations encountered during energy applications. The controller 224 utilizes the stored temperature variant electrode resistance R and thermal impedance $\Theta$, to calculate the actual RF current and power as represented in equations (III) and (IV).

In step 418, controller 224 calculates the RF voltage (V) and tissue impedance (Z) as a function of the RF current and RF power, which were previously calculated in steps 404 and 412, respectively. The calculation performed in step 418 may be performed using the formulas (VI) and (VII) below:

$$\text{RF Voltage}(V)=P/I_{rf} \qquad (VI)$$

$$\text{Tissue Impedance}(Z)=P/I^2_{rf} \qquad (VII)$$

In step 420, controller 224 processes either one or both of the calculated RF voltage (V) and the tissue impedance (Z) and controls the delivered energy to the tissue site in step 420, as a function of the generated radio frequency RF voltage or tissue impedance which were calculated in step 418. Differences in the sourced energy as measured by the sensor 229 and the delivered energy are adjusted in step 408, where an error signal is returned by the controller 224 to adjust the electrosurgical generator output 228 via power supply 227, represented in step 400, to correct the delivered RF voltage or tissue impedance for closed loop controlled delivery of the tissue treatment energy and effective hemostasis of tissue.

In step 422, controller 224 processes one or more of the RF power, voltage, current, tissue impedance, or combinations thereof to control the delivered energy to the tissue site, a function of the tissue temperature (T). Differences in the sourced energy as measured by the sensor 229 and the delivered energy are adjusted in step 408, where an error signal is returned by the controller 224 to adjust RF output of the generator 200 by controlling the output stage 228 and/or the power supply 227. In step 400, the controller 224 corrects the delivered RF energy for closed loop controlled delivery of the tissue treatment energy and effective hemostasis of tissue.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
an electrosurgical instrument including an electrode having a first connection, a second connection, and an active lead, each of which is electrically coupled to the electrode, the first and second connections configured to measure a voltage drop across the electrode; and
a generator including:
an output stage coupled to the electrode via the active lead, the output stage configured to generate radio frequency energy; and
a controller configured to calculate actual radio frequency current supplied to the tissue based on the measured voltage drop of the electrode and an electrical resistivity of the electrode.

2. The electrosurgical system according to claim 1, wherein the generator further includes a non-transitory storage medium readable by the controller, the non-transitory storage medium configured to store the electrical resistivity of the electrode.

3. The electrosurgical system according to claim 2, wherein the electrosurgical instrument further includes a thermal sensor coupled to the electrode, the thermal sensor configured to measure a temperature difference across electrode.

4. The electrosurgical system according to claim 3, wherein the non-transitory storage medium is configured to store thermal conductivity of the electrode.

5. The electrosurgical system according to claim 4, wherein the controller is further configured to determine power based on the measured temperature difference and the thermal conductivity of the electrode.

6. The electrosurgical system according to claim 5, wherein the controller is further configured to determine tissue impedance based on the calculated power and current.

7. The electrosurgical system according to claim 1, wherein the generator further includes at least one active output terminal coupled to the active lead and a return output terminal coupled to a return lead, the electrosurgical instrument is coupled to the active lead and the return lead, and the electrode is coupled to the generator through sensor leads electrically coupled to the first and second connections.

8. The electrosurgical system according to claim 7, further comprising:
an electrosurgical cable including a dielectric core, wherein the sensor leads are disposed within the dielectric core and at least a portion of each of the active lead and the return lead are wound in a double helix about the dielectric core to minimize an electrical field generated thereby.

9. An electrosurgical system, comprising:
an electrosurgical instrument including:
an electrosurgical instrument including an electrode having a first connection, a second connection, and an active lead, each of which is electrically coupled to the electrode, the first and second connections configured to measure a voltage drop across the electrode; and
a thermal sensor coupled to the electrode, the thermal sensor configured to measure a temperature difference across the electrode; and
a generator including:
an output stage coupled to the electrode via the active lead, the output stage configured to generate radio frequency energy; and
a controller configured to calculate actual radio frequency current supplied to the tissue based on the measured voltage drop of the electrode and an electrical resistivity of the electrode.

10. The electrosurgical system according to claim 9, wherein the generator further includes a non-transitory storage medium readable by the controller, the non-transitory storage medium configured to store the electrical resistivity value and thermal conductivity of the electrode.

11. The electrosurgical system according to claim 10, wherein the controller is further configured to determine power based on the measured temperature difference and the thermal conductivity of the electrode.

12. The electrosurgical system according to claim 11, wherein the controller is further configured to determine tissue impedance based on the calculated power and current.

13. The electrosurgical system according to claim 9, wherein the generator further includes at least one active output terminal coupled to the active lead and a return output terminal coupled to a return lead, the electrosurgical instrument is coupled to the active lead and the return lead, and each of the voltage and thermal sensors is coupled to the generator through a sensor lead.

14. The electrosurgical system according to claim 13, further comprising:
an electrosurgical cable including a dielectric core, wherein the sensor leads are disposed within the dielectric core and at least a portion of each of the active lead and the return lead are wound in a double helix about the dielectric core to minimize an electrical field generated thereby.

15. The electrosurgical system according to claim 9, wherein the electrosurgical instrument is an electrosurgical forceps including at least one shaft member having an end effector disposed at a distal end thereof, the end effector including two jaw members movable from a first position in spaced relation relative to one another to at least one subsequent position wherein the jaw members cooperate to grasp tissue therebetween, each of the jaw members including an electrically conductive sealing surface forming the electrode, wherein one electrically conductive sealing surface is coupled to the active lead and another electrically conductive sealing surface is coupled to the return lead.

16. The electrosurgical system according to claim 15, wherein the voltage and thermal sensors are disposed within at least one of the jaw members.

17. A method comprising:
measuring a voltage drop across an electrode of an electrosurgical instrument through a first connection electrically coupled to the electrode and a second connection electrically coupled the electrode, the electrosurgical instrument being coupled to a generator;
storing an electrical resistivity value of the electrode in a non-transitory storage medium readable by a controller; and
calculating actual radio frequency current supplied to the tissue based on the measured voltage drop of the electrode and the electrical resistivity of the electrode.

18. The method according to claim 17, further comprising:
storing a thermal conductivity value of the electrode in a non-transitory storage medium readable by a controller;
measuring temperature of the electrode; and
determining power based on the measured temperature difference and the thermal conductivity of the electrode.

19. The method according to claim 18, further comprising:
determining tissue impedance based on the calculated power and current.

* * * * *